US012593967B2

(12) United States Patent
Yamaki

(10) Patent No.: US 12,593,967 B2
(45) Date of Patent: Apr. 7, 2026

(54) ENDOSCOPE SYSTEM AND METHOD OF OPERATING THE SAME

(71) Applicant: FUJIFILM Corporation, Tokyo (JP)

(72) Inventor: Teppei Yamaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/812,983

(22) Filed: Aug. 22, 2024

(65) Prior Publication Data

US 2025/0072738 A1      Mar. 6, 2025

(30) Foreign Application Priority Data

Aug. 29, 2023      (JP) ................................. 2023-138933

(51) Int. Cl.
| | |
|---|---|
| *G02B 21/36* | (2006.01) |
| *A61B 1/045* | (2006.01) |
| *A61B 1/06* | (2006.01) |
| *H04N 23/71* | (2023.01) |
| *H04N 23/73* | (2023.01) |

(52) U.S. Cl.
CPC ............ *A61B 1/045* (2013.01); *A61B 1/0655* (2022.02); *H04N 23/71* (2023.01); *H04N 23/73* (2023.01)

(58) Field of Classification Search
CPC ... A61B 1/045; A61B 1/0655; A61B 1/00006; A61B 1/00009; H04N 23/71; H04N 23/73
See application file for complete search history.

(56) References Cited

U.S. PATENT DOCUMENTS

| | | | | |
|---|---|---|---|---|
| 2017/0196443 A1* | 7/2017 | Murakita | ................ | A61B 1/051 |
| 2019/0274530 A1* | 9/2019 | Ushiroda | ............. | G02B 21/365 |
| 2022/0151466 A1* | 5/2022 | Kashima | ............ | G02B 27/0075 |
| 2023/0029934 A1* | 2/2023 | Kamon | ................. | G06T 7/0012 |
| 2023/0418044 A1* | 12/2023 | Namba | ............. | G02B 23/2484 |

FOREIGN PATENT DOCUMENTS

JP            2019154680            9/2019

* cited by examiner

*Primary Examiner* — Howard D Brown, Jr.
(74) *Attorney, Agent, or Firm* — JCIPRNET

(57) ABSTRACT

An endoscope system includes a processor, in which the processor performs exposure amount control based on an endoscope image captured by an endoscope including an imaging element, calculates brightness information indicating a degree of brightness of an edge portion of the endoscope image, and controls a tracking speed of the exposure amount control according to the brightness information. The brightness information is compared with past brightness information, which is the brightness information in the past, and a suppression coefficient for suppressing a change amount or a change rate of an exposure amount, which is decided according to a comparison result, is applied to the exposure amount control to control the tracking speed.

12 Claims, 11 Drawing Sheets

| CONTROL CYCLE | BRIGHTNESS INFORMATION | PAST BRIGHTNESS INFORMATION (COMPARISON VALUE) | PAST BRIGHTNESS INFORMATION (UPDATED VALUE) |
|---|---|---|---|
| T (1) | D (1) | PREDETERMINED VALUE | $Dp(1) = D(1)$ |
| T (2) | D (2) | Dp (1) | $Dp(2) = \dfrac{D(2)}{4} + \dfrac{3Dp(1)}{4}$ |
| T (3) | D (3) | Dp (2) | $Dp(3) = \dfrac{D(3)}{4} + \dfrac{3Dp(2)}{4}$ |
| ... | ... | ... | ... |
| T (n) | D (n) | Dp (n−1) | $Dp(n) = \dfrac{D(n)}{4} + \dfrac{3Dp(n-1)}{4}$ |
| T (n+1) | D (n+1) | Dp (n) | $Dp(n+1) = \dfrac{D(n+1)}{4} + \dfrac{3Dp(n)}{4}$ |
| ... | | | ... |

TRACKING SPEED CHANGE

ENDOSCOPE SYSTEM AND METHOD OF OPERATING THE SAME

CROSS-REFERENCE TO RELATED APPLICATIONS

This application claims priority under 35 U.S.C § 119 (a) to Japanese Patent Application No. 2023-138933 filed on 29 Aug. 2023. The above application is hereby expressly incorporated by reference, in its entirety, into the present application.

BACKGROUND OF THE INVENTION

1. Field of the Invention

The present invention relates to an endoscope system and a method of operating the same.

2. Description of the Related Art

In recent years, in a medical field, in a system that acquires an image and observes a target, dimming control for making an image showing the observation target have optimal brightness is widely used. In such dimming control, brightness information of the image is calculated based on a brightness value of the image, and an amount of emitted light or an imaging parameter of an imaging device is changed such that the brightness information is a target value.

In a case of the above-described dimming control, even in a case in which the brightness of the observation target in a screen being observed by a user is optimal, the brightness of the image may be determined to be different from the optimal value due to an influence of a disturbance such as reflection of light, and the amount of emitted light or the imaging parameter of the imaging device may unintentionally fluctuate. In order to suppress the unintended fluctuation, a technique of switching dimming control according to a change in an observation visual field or the like has been developed, and a medical dimming control device disclosed in JP2019-154680A is known as an example.

In the medical dimming device of JP2019-154680A (corresponding to US2019/0274530A1), in a case in which a change operation of an observation visual field or an imaging condition is performed, an image having an optimal brightness can be quickly acquired by performing the dimming control at a fast tracking speed, and after the image having the optimal brightness is obtained, the tracking speed is switched to a slow tracking speed, so that the tracking of the unintended brightness fluctuation is stopped, and the user can perform the observation in a state in which the dimming is matched to the target that the user really wants to observe.

SUMMARY OF THE INVENTION

In JP2019-154680A, the dimming control is performed assuming a state in which the observation visual field is difficult to fluctuate after the observation visual field is changed once, like a microscope image, and a state in which a distance to the observation target frequently fluctuates as in a case of an endoscope is not assumed. For example, in a case in which a part of an image has halation because a fold of an organ or the like is reflected on a screen edge during observation with an endoscope, the operation is performed in a mode with fast tracking performance, and thus tracks the unintended brightness fluctuation, which is halation at an image edge. As a result, the image is darkened by the dimming control even though the observation target has appropriate brightness, so that the user cannot perform the observation with appropriate brightness.

An object of the present invention is to provide an endoscope system that performs imaging with appropriate brightness in a state in which a distance to an observation target frequently fluctuates, and a method of operating the same.

An endoscope system according to an aspect of the present invention comprises: a processor, in which the processor performs exposure amount control based on an endoscope image captured by an endoscope including an imaging element, calculates brightness information indicating a degree of brightness of an edge portion of the endoscope image, and controls a tracking speed of the exposure amount control based on the brightness information.

It is preferable that the processor calculates a suppression coefficient for suppressing a change amount or a change rate of an exposure amount in the exposure amount control based on the brightness information, and applies the suppression coefficient to the exposure amount control to control the tracking speed.

It is preferable that the processor decides the suppression coefficient according to a comparison result of past brightness information, which is the brightness information in the past, and the brightness information.

It is preferable that the processor calculates the suppression coefficient in a case in which the brightness information is larger than the past brightness information in the comparison result.

It is preferable that the processor sets the suppression coefficient to a lower limit value in a case in which the brightness information is equal to or less than the past brightness information in the comparison result.

It is preferable that the processor holds a pre-change suppression coefficient, which is the suppression coefficient used for calculating the tracking speed before change, and performs correction of the suppression coefficient in a case in which the suppression coefficient is smaller than the pre-change suppression coefficient.

It is preferable that the processor performs a change of bringing the tracking speed closer to a reference state in a stepwise manner as the correction.

It is preferable that the processor sets the suppression coefficient to the lower limit value in a case in which the suppression coefficient is equal to or less than a preset threshold value.

It is preferable that the processor updates the past brightness information by using the calculated brightness information and a plurality of pieces of the past brightness information held.

It is preferable that the processor calculates the brightness information from a difference in brightness between a central portion of the endoscope image and the edge portion of the endoscope image.

It is preferable that the processor decides the brightness information based on an amount of high-brightness pixels, which are pixels having a brightness value equal to or greater than a preset threshold value.

It is preferable that the processor changes at least any of an amount of illumination light or an imaging parameter of the imaging element based on the brightness information as the exposure amount control.

A method of operating an endoscope system according to another aspect of the present invention comprises: a step of capturing an endoscope image based on exposure amount control; a step of calculating brightness information indicating a degree of brightness of an edge portion of the endoscope image; and a step of controlling a tracking speed of the exposure amount control according to the brightness information.

According to the present invention, it is possible to perform imaging with appropriate brightness in a state in which a distance to an observation target frequently fluctuates, and a method of operating the same.

BRIEF DESCRIPTION OF THE DRAWINGS

FIG. 2 is a block diagram showing a function of the endoscope system.

FIG. 6 is an explanatory diagram for comparing brightness information and updating past brightness information in each control cycle.

FIGS. 11A and 11B are modification examples, in which FIG. 11A is an explanatory diagram of an edge portion image in which an edge portion is set narrower than in an example, and FIG. 11B is an explanatory diagram of an edge portion image in which the edge portion is set wider than in the example.

DESCRIPTION OF THE PREFERRED EMBODIMENTS

Figure 1:
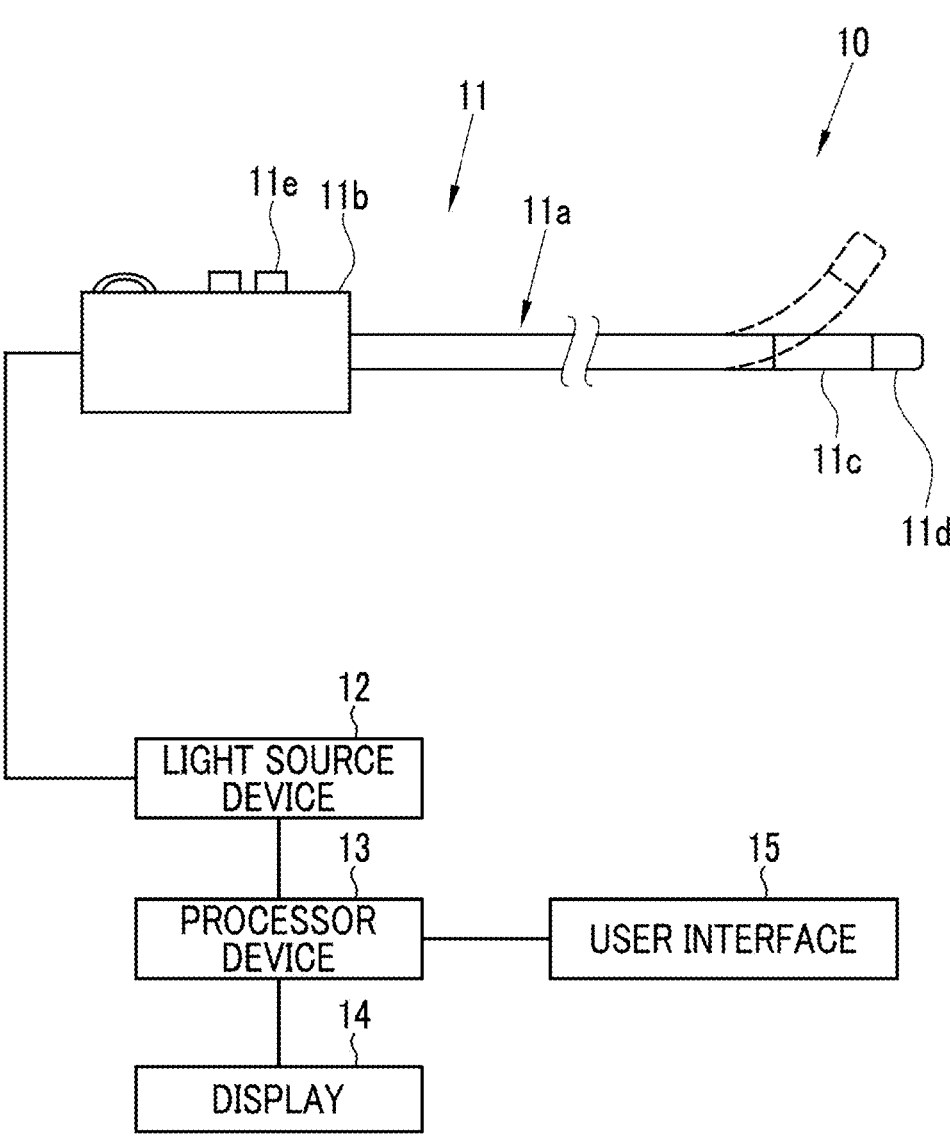
FIG. 1 is a schematic view of an endoscope system.

As shown in FIG. 1, an endoscope system 10 according to an embodiment of the present invention includes an endoscope 11, a light source device 12, a processor device 13, a display 14, and a user interface (UI) 15. The endoscope 11 is optically connected to the light source device 12 and electrically connected to the processor device 13. The light source device 12 supplies illumination light to the endoscope 11.

The endoscope 11 emits illumination light and images an observation target to acquire an endoscope image. The endoscope 11 has an insertion part 11a that is to be inserted into a living body (inside an object to be examined) having the observation target, and an operation part 11b that is provided at a base end portion of the insertion part 11a. A bendable part 11c and a distal end part 11d are provided on a distal end side of the insertion part 11a. The bendable part 11c is operated by the operation part 11b to be bent in a desired direction. The distal end part 11d irradiates the observation target with illumination light and receives reflected light from the observation target to image the observation target. The operation part 11b is provided with a mode selector switch 11e that is used for an operation for switching a mode.

The processor device 13 is electrically connected to the display 14 and the user interface 15. The processor device 13 receives an image signal from the endoscope 11, and performs various kinds of processing based on the image signal. An external recording medium (not shown), which records an image, image information, and the like, may be connected to the processor device 13. The display 14 outputs and displays a captured image of the observation target, image information, and the like, which have been image-processed by the processor device 13. The user interface 15 includes a keyboard, a mouse, a touch pad, a microphone, a foot pedal, and the like, and has a function of receiving an input operation such as function setting.

The endoscope system 10 can execute normal observation for observing an observation site and special observation for enhancing and observing a specific structure in the observation site. In the special observation, a plurality of frames including a frame illuminated with illumination light of a specific wavelength to enhance a specific structure are imaged to generate one observation image. The generated observation image is displayed on the display 14. In a case in which no particular designation is made, exposure amount control is performed in a normal mode and a tracking control mode during the normal observation.

Figure 2:
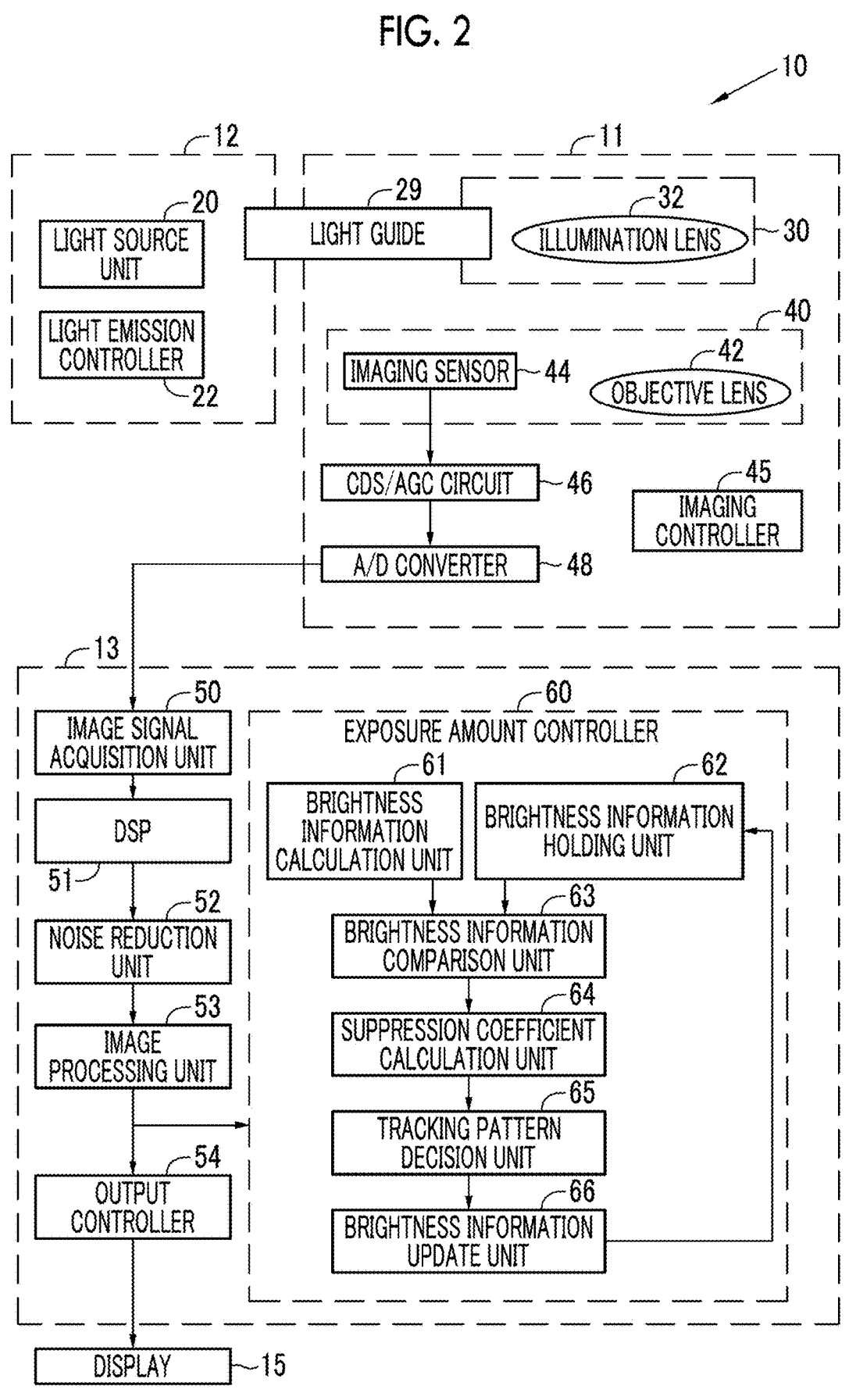

As shown in FIG. 2, in the endoscope system 10, the light source device 12 propagates emitted illumination light to the endoscope 11 via a light guide 29, the endoscope 11 transmits an image signal imaged using illumination light to the processor device 13, and the processor device 13 generates an image to be displayed on the display 14.

The light source device 12 comprises a light source unit 20 that emits one or a plurality of illumination light beams, and a light emission controller 22 that generates a drive current (drive signal) for controlling a light emission timing, a light emission amount, and the like of the light source unit 20 and that supplies the drive current to the light source unit 20 to cause the light source unit 20 to emit light. The function of the light emission controller 22 is realized by a light source control processor (not shown) included in the light source device 12, and the light emission controller 22 supplies a drive current (drive signal) for controlling the light emission timing, the amount of illumination light, and the like to the light source unit 20 to control the illumination light to be emitted in response to reception of a light emission control signal. In a case in which the light source device 12 and the processor device 13 are electrically connected, the function of the light source control processor may be realized by a central controller instead of the light source control processor.

In the light source device 12, the light emission controller 22 performs light emission and light amount control according to the drive current to be transmitted to the light source unit 20. A magnitude of the light amount in light emission is decided based on a drive current value. The light emission controller 22 stores a target light emission amount or a target light emission timing, or receives an input from the processor device 13. The light emission amount indicates a magnitude of light output emitted per unit time.

In light emission in one frame, brightness information based on the endoscope image can be calculated as the amount of light received by an imaging sensor 44. Since the light emission of each frame is controlled to be stopped in a case in which the amount of light reaches a preset amount of light required for the imaging, the imaging can be performed with brightness suitable for observation. In a case in which the light source 25 emits light, a drive current having a predetermined drive current value is transmitted from the light emission controller 22 to the light source 25, so that the light source 25 emits light with the amount of light emission corresponding to the drive current. The amount of light emission and the drive current value have a proportional relationship.

The light emitted from the light source unit 20 is incident into the light guide 29. The light guide 29 is built in the endoscope 11 and a universal cord (a cord connecting the endoscope 11, the light source device 12, and the processor device 13). The light guide 29 propagates the light from the light source unit 20 to the distal end part 11d of the endoscope 11.

An illumination optical system 30 and an imaging optical system 40 are provided at the distal end part 11d of the endoscope 11. The illumination optical system 30 has an illumination lens 32, and the illumination light propagated by the light guide 29 is applied to the observation target via the illumination lens 32. The imaging optical system 40 includes an objective lens 42 and an imaging sensor 44. Reflected light of the illumination light returning from the observation target irradiated with the illumination light is incident into the imaging sensor 44, which is a color imaging sensor, via the objective lens 42. As a result, an image of the observation target is formed on the imaging sensor 44.

As the imaging sensor 44, a photoelectric conversion element such as a charge coupled device (CCD) sensor or a complementary metal-oxide semiconductor (CMOS) sensor is used. The imaging sensor 44 performs, for example, an accumulation operation of performing photoelectric conversion of received light and accumulating signal charges corresponding to the amount of received light for each pixel and a readout operation of reading out the accumulated signal charges, within an acquisition period of one frame. The signal charge for each pixel read out from the imaging sensor 44 is converted into a voltage signal and is input to a correlated double sampling/automatic gain control (CDS/AGC) circuit 46. The light source device 12 generates illumination light in accordance with a timing of the accumulation operation of the imaging sensor 44 and causes the illumination light to be incident into the light guide 29.

Each pixel of the imaging sensor 44 is provided with any of a blue pixel (B pixel) having a blue (B) color filter, a green pixel (G pixel) having a green (G) color filter, or a red pixel (R pixel) having a red (R) color filter. For example, the imaging sensor 44 is preferably a color imaging sensor of a Bayer array in which a ratio of the number of pixels of the B pixels, the G pixels, and the R pixels is 1:2:1.

The B color filter mainly transmits light in a blue band, specifically, light of which a wavelength range is 380 to 560 nm (blue transmission range). A peak wavelength at which a transmittance is maximized exists around 460 to 470 nm. The G color filter mainly transmits light in a green band, specifically, light of which a wavelength range is 450 to 630 nm (green transmission range). The R color filter mainly transmits light in a red band, specifically, light of which a wavelength range is 580 to 760 nm (red transmission range).

In addition, a complementary color imaging sensor comprising complementary color filters corresponding to cyan (C), magenta (M), yellow (Y), and green (G) may be used instead of the primary color imaging sensor 44. In a case in which the complementary color imaging sensor is used, image signals corresponding to four colors of C, M, Y, and G are output. Therefore, in a case in which the image signals corresponding to four colors of C, M, Y, and G are converted into image signals corresponding to three colors of R, G, and B by complementary color-primary color conversion, image signals corresponding to the same respective colors of R, G, and B as those of the imaging sensor 44 can be obtained.

An imaging controller 45 drives and controls the imaging sensor 44 according to a signal from the light emission controller 22 via the mode selector switch 11e, an instruction input from the user interface 15 via the processor device 13, or the like, and switches between the normal mode and the tracking control mode with respect to the exposure amount control and control the imaging in each mode. In the control of the imaging, adjustment of an exposure period through setting of a shutter speed of an electronic shutter (not shown) of the imaging sensor 44 is performed. In addition, the control signal is transmitted to the light emission controller 22 to control the amount of light emission and the light emission timing of the illumination light in the light source device 12. The instruction input from the user interface 15 includes setting using a menu screen or an operation button displayed on the display 14. In addition, an internal parameter such as an upper limit value of the amount of emitted light, which is decided by the type of scope in the endoscope 11, may be used for the exposure amount control.

The CDS/AGC circuit 46 performs correlated double sampling (CDS) or automatic gain control (AGC) on the analog image signals obtained from the imaging sensor 44. The image signal that has passed through the CDS/AGC circuit 46 is converted into a digital image signal by an analog/digital (A/D) converter 48. The digital image signal after the A/D conversion is input to the processor device 13.

In the processor device 13, a program related to each processing is incorporated in a program memory (not shown). In a case in which a central controller (not shown) configured by a processor executes the program in the program memory, functions of an image signal acquisition unit 50, a digital signal processor (DSP) 51, a noise reduction unit 52, an image processing unit 53, an output controller 54, and an exposure amount controller 60 are realized. In addition, the exposure amount controller 60 has functions of a brightness information calculation unit 61, a brightness information holding unit 62, a brightness information comparison unit 63, a suppression coefficient calculation unit 64, a tracking pattern decision unit 65, and a brightness information update unit 66.

The image signal acquisition unit 50 receives an image signal input from the endoscope 11, which is subjected to a drive control by the imaging controller 45, and transmits the received image signal to the DSP 51. The output controller 54 transmits an image signal of an image to be displayed, which is acquired from the image processing unit 53, to the display 14.

The DSP 51 performs various kinds of signal processing, such as defect correction processing, offset processing, gain correction processing, linear matrix processing, gamma conversion processing, demosaicing, and YC conversion processing, on the received image signal. In the defect correction processing, a signal of a defective pixel of the imaging sensor 44 is corrected. In the offset processing, a dark current component is removed from the image signal that has passed through the defect correction processing, and an accurate zero level is set. In the gain correction processing, a signal level of each image signal is adjusted by multiplying the image signal of each color after the offset processing by a specific gain. The image signal of each color after the gain correction processing is subjected to the linear matrix processing for enhancing color reproducibility.

After that, brightness and chroma saturation of each image signal are adjusted by the gamma conversion processing. The image signal after the linear matrix processing is subjected to the demosaicing (also referred to as isotropic processing or synchronization), and a signal of a color missing from each pixel is generated by interpolation. By the demosaicing, all pixels have signals of respective colors of R, G, and B. The DSP 51 performs the YC conversion processing on each image signal after the demosaicing, and outputs a brightness signal Y, a color difference signal Cb, and a color difference signal Cr to the noise reduction unit 52.

The noise reduction unit 52 performs noise reduction processing by, for example, a moving average method or a median filter method on the image signal that has passed through the demosaicing or the like by the DSP 51. The image signal with reduced noise is input to the image processing unit 53.

The image processing unit 53 performs color conversion processing, such as 3×3 matrix processing, gradation transformation processing, and three-dimensional look up table (LUT) processing, on the image signal for one frame input from the noise reduction unit 52. Then, various kinds of color enhancement processing are performed on the RGB image data that has been subjected to the color conversion processing. Structure enhancement processing such as spatial frequency enhancement is performed on the RGB image data that has been subjected to the color enhancement processing. The RGB image data that has been subjected to the structure enhancement processing is input to the output controller 54 as the observation image.

The output controller 54 sequentially acquires the observation images from the image processing unit 53, and converts the acquired observation images into video signals that enable full-color display on the display 14. The converted video signal is output to and displayed on the display 14. Accordingly, a doctor or the like can observe the observation target by using a still image or a video image of the observation image.

The exposure amount controller 60 calculates brightness information for the observation image generated by the image processing unit 53 and performs exposure amount control according to the brightness information. At least one of the light emission control of the light source device 12 or the light reception control of the endoscope 11 is executed as the exposure amount control. Via the output controller 54, a light control signal is transmitted to the light emission controller 22 and an imaging control signal is transmitted to the imaging controller 45.

In the exposure amount control, at least any of the amount of illumination light emitted from the light source unit 20 or the imaging parameter of the imaging element included in the imaging sensor 44 is changed based on the brightness information. In addition, it is preferable to control the light emission timing and the exposure time. In a case in which the exposure amount is decreased in the change of the imaging parameter, the sensitivity of the imaging element is weakened or the exposure time is shortened. The adjustment of the length of the exposure time is performed, for example, by changing the shutter speed of the electronic shutter to change the length of the imaging frame. In addition, it is preferable that opening and closing of the shutter is controlled in synchronization with the imaging frame.

The brightness information calculation unit 61 calculates an evaluation value for allowing the brightness in the endoscope image generated by the image processing unit 53 to be digitized or evaluated in a comparable grade. The brightness of each pixel in the endoscope image is calculated, and distribution data of the brightness is created. The brightness is preferably evaluated in 256 stages. Instead of the brightness, lightness which is evaluated in 10 stages may be used. Although the calculation of the brightness information is linked with the acquisition timing of the observation image generated from the frame image, the calculation may be performed once for a plurality of frames instead of every single frame.

The brightness information holding unit 62 holds the calculated brightness information as past brightness information. The past brightness information is used for the comparison in the brightness information comparison unit 63. The past brightness information includes the calculated brightness information held individually, and brightness information calculated and held by the brightness information update unit 66 using a plurality of pieces of brightness information. In addition, the brightness information holding unit 62 also holds a predetermined value of the brightness information used for the comparison in a case in which the past brightness information is not accumulated, or the like.

The brightness information comparison unit 63 compares the calculated brightness information with a predetermined value or the past brightness information. In the comparison, the brightness information calculated by the brightness information calculation unit 61 and the predetermined value or the past brightness information held by the brightness information holding unit 62 are used.

The suppression coefficient calculation unit 64 calculates a suppression coefficient based on a comparison result of the brightness information. The suppression coefficient is a coefficient for delaying the tracking speed in the exposure amount control, and the tracking speed decreases as the suppression coefficient is set to a larger value. In a case in which the calculated brightness information is not brighter than the predetermined value or the past brightness information, the suppression coefficient is reset to a lower limit value. The predetermined value is a preset threshold value or the like. In a case in which it is determined that the calculated brightness information is brighter than the predetermined value or the past brightness information, a suppression coefficient based on the comparison result is calculated.

The tracking pattern decision unit 65 decides a tracking pattern in the exposure amount control based on the suppression coefficient calculated by the suppression coefficient calculation unit 64. In a case in which the suppression coefficient is 1, there is no delay correction, so that the exposure amount control is performed in a reference state with the same tracking pattern as in the normal observation. The tracking speed is changed each time the suppression coefficient is acquired from the suppression coefficient calculation unit 64, but a pre-change suppression coefficient, which is the suppression coefficient used for calculating the tracking speed before change, is held even after the change of the tracking speed. In a case in which a value of a suppression coefficient newly acquired is smaller than the pre-change suppression coefficient, the suppression coefficient is corrected. As the correction, a change of bringing the tracking speed closer to the reference state in a stepwise manner is performed.

The brightness information update unit 66 updates the past brightness information by using the calculated brightness information. The brightness information calculated by the brightness information calculation unit 61 and the plurality of pieces of past brightness information held by the brightness information holding unit 62 are used to update the past brightness information. For example, the update is performed based on an infinite impulse response calculated using an infinite impulse response (IIR) filter. In addition, only a moving average of the brightness information calculated in the past or the brightness information calculated immediately before may be used as the past brightness information.

An example of using the endoscope system 10 according to the present embodiment described above will be described. The exposure amount controller 60 has two types of modes, that is, a normal mode in which the exposure amount is controlled at a fixed tracking speed and the observation is performed, and a tracking control mode in which the exposure amount is controlled at a tracking speed based on the calculated brightness information and the observation is performed, as an observation mode. The observation mode is optionally switched by a user operation with respect to any of the endoscope 11, the processor device 13, or the light source device 12.

In the normal mode, a normal observation image is captured with an appropriate exposure amount for the overall observation of the observation site. In the normal observation, the light is continuously turned on during the observation, and the exposure period is adjusted by the opening and closing of the shutter or the like. In the normal mode, the exposure amount control is executed based on the brightness information at a fixed reference state tracking speed. In the tracking control mode, the exposure amount control is executed at a tracking speed based on the suppression coefficient calculated from the brightness information.

In the tracking control mode, the exposure amount control is performed based on the endoscope image captured by the endoscope 11, the brightness information indicating the degree of brightness of the endoscope image is calculated, and the tracking speed of the exposure amount control is changed based on the brightness information. The brightness information is calculated using, for example, a brightness value of a pixel in the endoscope image.

Since the suppression coefficient used for changing the tracking speed is decided by using the past brightness information, the tracking speed of the tracking control mode immediately after the switching is set as a reference state in which the delay does not occur as in the normal mode, and the reset of the tracking speed, which will be described below, refers to changing to the reference state. The suppression coefficient in the reference state is 1 as a lower limit value. The suppression coefficient is calculated based on the brightness information, and the calculated suppression coefficient is applied to the exposure amount control to control the tracking speed. For example, the tracking speed is delayed from the reference state. The suppression coefficient is decided according to the comparison result of the past brightness information, which is the brightness information in the past, and the calculated brightness information. In the comparison result, in a case in which the brightness information is larger than the past brightness information, the suppression coefficient is calculated. The change amount or the change rate of the exposure amount in the exposure amount control is suppressed based on the suppression coefficient.

In the tracking control mode, the brightness information of the captured endoscope image is calculated, and the tracking speed of the exposure amount control is changed according to the brightness information. The tracking speed is delayed with respect to the reference state based on the suppression coefficient calculated using the brightness information.

Figure 3:
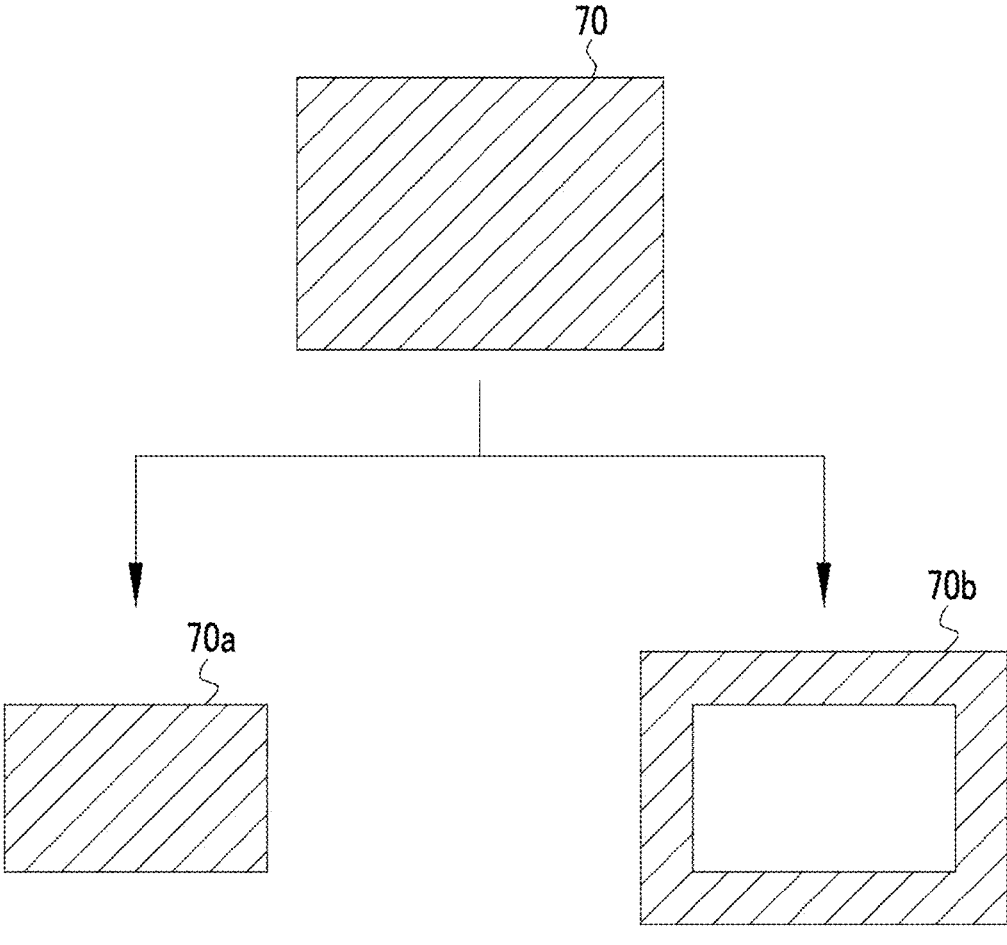
FIG. 3 is an explanatory diagram for calculating brightness information by dividing an endoscope image into a central portion image and an edge portion image.

As shown in FIG. 3, the brightness information is calculated by using an endoscope image 70 captured by the endoscope 11. In the calculation of the brightness information, the exposure amount controller 60 uses the brightness value of each pixel of the endoscope image divided into two regions. The two regions are a central portion image 70*a* obtained by extracting a region of a central portion from the endoscope image 70 and an edge portion image 70*b* obtained by extracting a region of an edge portion from the endoscope image 70, and the brightness information is calculated using a difference in the number of high-brightness pixels as a difference in brightness between the central portion image 70*a* and the edge portion image 70*b*. It is preferable that an area ratio of the central portion image 70*a* to the edge portion image 70*b* is 1:1, that is, the same number of pixels.

By comparing the brightness information of the entire endoscope image 70 or the central portion image 70*a* with the brightness information of the edge portion image 70*b*, the exposure amount control is performed by discriminating an appropriate situation, such as a case in which only the edge portion is clearly bright or a case in which a foreign substance such as a fold with a high reflectivity is reflected. The brightness information is decided based on an amount of high-brightness pixels, which are pixels having a brightness value equal to or greater than a preset threshold value for high brightness discrimination.

Figure 4A:
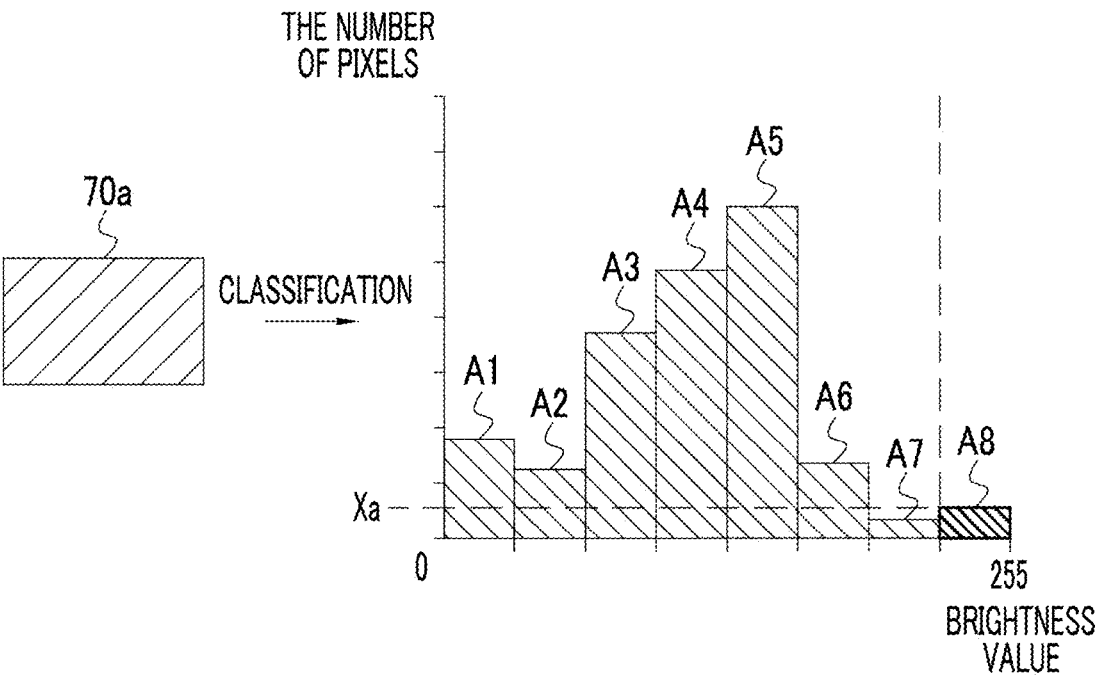
FIG. 4A is an explanatory diagram showing classification according to a brightness value of a pixel of the central portion image.
Figure 4B:
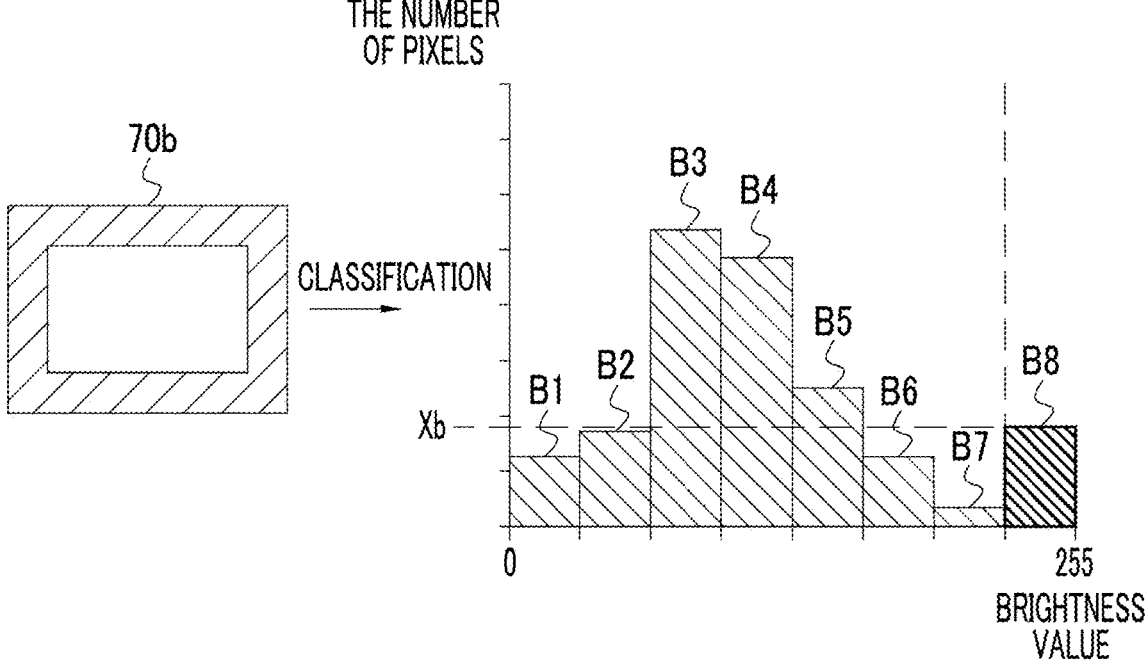
FIG. 4B is an explanatory diagram showing classification according to a brightness value of a pixel of the edge portion image.

As shown in FIGS. 4A and 4B, the brightness information calculation unit 61 discriminates a brightness value of each pixel of the central portion image 70*a* and the edge portion image 70*b* extracted from the endoscope image 70. The brightness value takes any value from 0 to 255 in 256 gradations, and the numerical value is higher as the brightness is higher. FIG. 4A is a histogram showing a distribution of the brightness values in the central portion image 70*a*, in which a vertical axis represents the number of pixels and a horizontal axis represents the brightness value. In the histogram, the brightness values are classified into eight stages. FIG. 4B is a histogram showing a distribution of the brightness values in the edge portion image 70*b*, and can be compared with FIG. 4A. A pixel classified into a group having the highest brightness value in each histogram is discriminated as a high-brightness pixel.

For example, in FIG. 4A, in a case in which pixel values of the central portion image 70*a* are divided into eight groups A1 to A8, the group A1 is classified into 0 to 34, the group A2 is classified into 35 to 69, the group A3 is classified into 70 to 104, the group A4 is classified into 105 to 139, the group A5 is classified into 140 to 174, the group A6 is classified into 175 to 209, the group A7 is classified into 210 to 244, and the group A8 is classified into 245 to 255. A pixel classified into the group A8, that is, a pixel having the brightness value of 224 or more may be defined as the high-brightness pixel. The division interval may be further finely divided instead of 8 divisions.

In addition, the grouping of the pixel values of the edge portion image 70*b* in FIG. 4B is executed by the same method as the central portion image 70*a*. That is, a group B1 corresponds to the group A1, a group B2 corresponds to the group A2, a group B3 corresponds to the group A3, a group B4 corresponds to the group A4, a group B5 corresponds to the group A5, a group B6 corresponds to the group A6, a group B7 corresponds to the group A7, and a group B8 corresponds to the group A8.

The comparison based on the distribution of the brightness values can be used not only for discrimination of a foreign substance, which will be described below, but also for normal light amount control in the progress of the endoscopic observation. For example, in a case in which the groups A1 to A3 and the groups B1 to B3 have a large number of pixels, it can be discriminated that the exposure amount of the entire endoscope image 70 is insufficient, and control is performed to change the imaging parameter to increase the amount of light emitted from the light source unit 20 or to increase the light-receiving sensitivity in the imaging optical system 40.

Instead of the grouping, a threshold value for high brightness discrimination may be set such that a pixel having the brightness value of 245 or more and a pixel having a brightness value of 250 or more are set as the high-brightness pixel, and a pixel having a brightness value equal to or greater than the threshold value for high brightness discrimination may only be set as the high-brightness pixel. The threshold value for high brightness discrimination may be changed by the user through the operation via the user interface 15.

Figure 5:
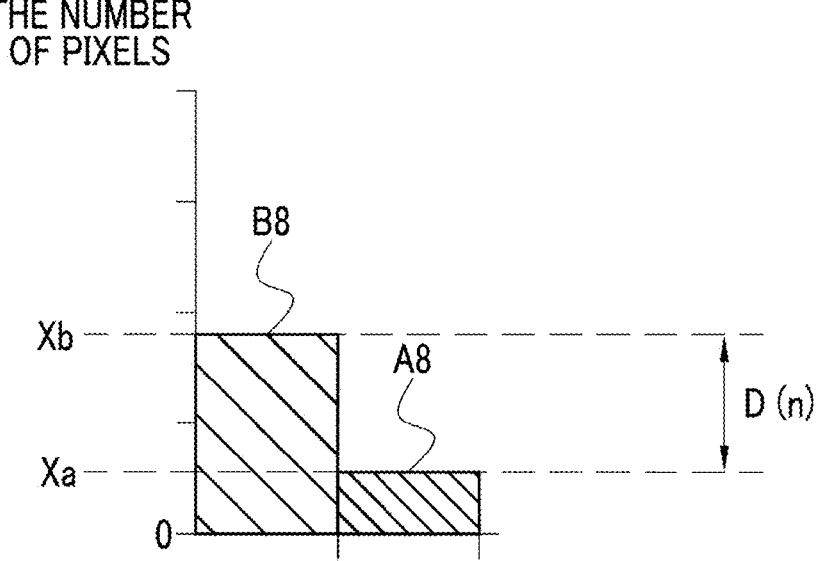
FIG. 5 is an explanatory diagram for calculating a difference between the number of high-brightness pixels in the edge portion image and the number of high-brightness pixels in the central portion image.

As shown in FIG. 5, brightness information D(n) of the endoscope image 70 can be decided from a difference value between Xa, which is the number of central portion high-brightness pixels, and Xb, which is the number of edge portion high-brightness pixels. The brightness information D(n) is a difference value calculated in n-th brightness information calculation in the tracking control mode. In a case in which the number of pixels of A8 in FIG. 4A is set to the number of central portion high-brightness pixels, which is the number of high-brightness pixels of the central portion image 70*a*, the number of pixels of B8 in FIG. 4B is set to the number of edge portion high-brightness pixels, which is the number of pixels of the edge portion image 70*b*, and the number of central portion high-brightness pixels is defined as Xa and the number of edge portion high-brightness pixels is defined as Xb, the brightness information D(n) is a value of Xb–Xa. As the value of the brightness information D(n) is a larger value with a positive number, it can be determined that the edge portion of the endoscope image 70 is brighter than the central portion.

In order to discriminate that the edge portion image 70*b* is brighter than the central portion image 70*a*, it is preferable to provide a reference for discriminating whether or not the brightness is significant based on the number of pixels of the endoscope image 70 in addition to the fact that the value of the brightness information D(n) is a positive number (0<D (n)). For example, in a case in which the value of the brightness information D(n), which is the difference value, is less than 1% of the number of pixels of the endoscope image 70, it is determined that the brightness is not significant, and D(n) is approximated to 0.

A suppression coefficient for suppressing the exposure amount control that tracks the unintended brightness fluctuation such as halation that occurs in a state in which a foreign substance is reflected is calculated. The calculation of the suppression coefficient to be used for the tracking pattern is performed under the condition that the value of the brightness information D(n) in a state in which the number of the high-brightness pixels in the edge portion image 70*b* is larger than the number of the high-brightness pixels in the central portion image 70*a* is a positive number and the brightness information D(n) is brighter than the past brightness information.

As shown in FIG. 6, in the brightness information comparison, the calculated brightness information is compared with the past brightness information updated in the previous control cycle. In the tracking control mode, a cycle of performing the brightness information calculation for the endoscope image, the calculation of the suppression coefficient, the change of the tracking speed, and the update of the brightness information is used as a control cycle to perform the exposure amount control. A control cycle T(1) in which the first brightness information calculation is performed, that is, immediately after the switching to the tracking control mode, a control cycle T(2) next to the control cycle T(1), a control cycle T(3) next to the control cycle T(2), and a control cycle T(n) in which n-th brightness information calculation is performed at any number of times are set.

The past brightness information updated and held in the control cycle T(n) is defined as past brightness information Dp(n). That is, in the control cycle T(n), the calculated brightness information D(n) is compared with past brightness information Dp(n−1) which is a comparison value, and the possibility of calculating the suppression coefficient is decided according to the comparison result. Note that, since the past brightness information Dp(n) is not held in the control cycle T(1), a predetermined value is used as the comparison value. In addition, since the past brightness information Dp(n) uses a larger number of pieces of the calculated brightness information D(n) as the value of n increases, the comparison with the predetermined value may be performed even in a case in which the number of times of the control cycle T(n) is equal to or less than a preset reference number. The predetermined value is brightness information measured in another endoscopic observation, or the like.

The brightness information used for the comparison is used for updating the past brightness information. The past brightness information is updated, for example, by using an infinite impulse response using an IIR filter. In the infinite impulse response, Expression (1) is used in which the brightness information calculated in the control cycle T(n) is represented by D(n), and the past brightness information updated in the control cycle T(n) is represented by the past brightness information Dp(n).

$$Dp(n) = \left(D(n)/4\right) + \left(3Dp(n-1)/4\right) \tag{1}$$

As shown in Expression (1), the past brightness information Dp(n) to be updated in the control cycle T(n) is a sum of ¼ of the brightness information calculated in the control cycle T(n) and ¾ of the past brightness information Dp(n−1) updated in the control cycle T(n−1). As a result, in the control cycle T(n+1), even though the endoscope image 70 in which continuous halation is caused is acquired, it can be discriminated that it is brighter than the past brightness information every time, and in a case in which the endoscope image 70 in which halation is not caused is acquired, it can be discriminated that it is not brighter than the past brightness information. Past brightness information Dp(n+1), which is an updated value, is calculated and updated regardless of the discrimination result.

In a case in which the difference value obtained by calculating the brightness information of the control cycle T(n), which is brighter than the past brightness information, is defined as D(n), the suppression coefficient is calculated in a case in which Expression (2) is satisfied.

$$D(n) - Dp(n-1) > 0 \qquad (2)$$

In a case in which Expression (2) is satisfied and it is determined in the comparison that the brightness information D(n) is brighter than the past brightness information Dp(n−1), the suppression coefficient is calculated using the comparison result. In a case in which Expression (2) is not satisfied and it is not determined that the brightness information is brighter than the past brightness information, the suppression coefficient is set to 1, which is a lower limit value. The reset of the suppression coefficient refers to changing the suppression coefficient to 1. On the other hand, in a case in which the brightness information D(n) is a number equal to or less than 0, or in a case in which the brightness information based on the brightness information D(n) is equal to or less than the past brightness information, the suppression coefficient is set to 1, which is the lower limit value.

Figure 7:
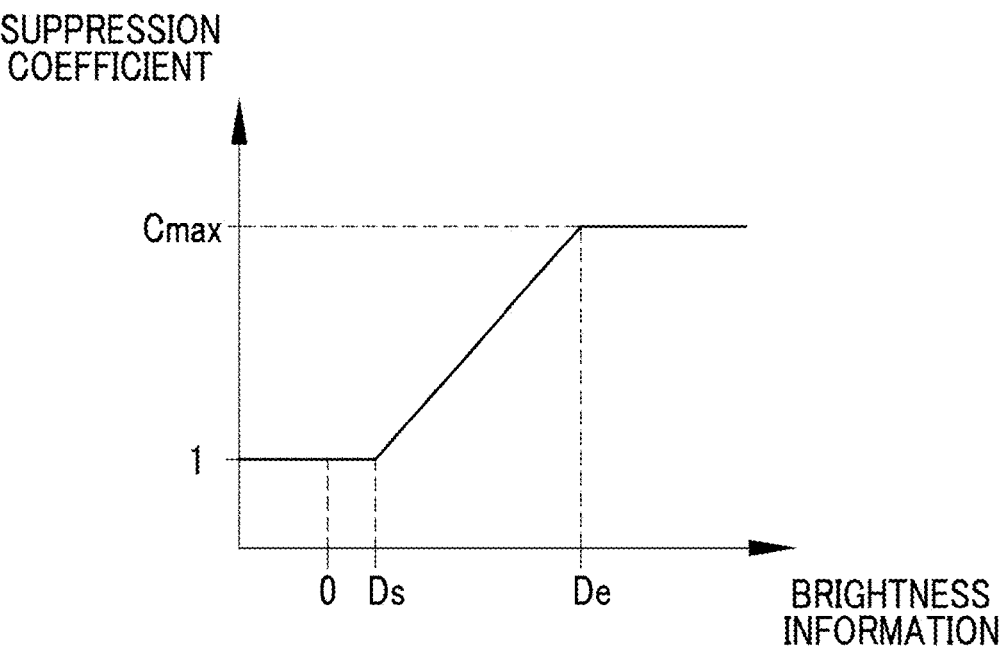
FIG. 7 is an explanatory diagram showing a relationship between a suppression coefficient used for a tracking speed of exposure amount control and brightness information.

As shown in FIG. 7, a suppression coefficient C for deciding the tracking pattern is calculated by using the brightness information D(n). The suppression coefficient C is calculated in a case in which the brightness information D(n) takes a lower limit threshold value Ds to an upper limit threshold value De as a predetermined range. The suppression coefficient C in a case in which the brightness information is equal to or less than the lower limit threshold value Ds is 1 as the lower limit value, and the exposure amount control is performed in the same tracking pattern as in the normal mode. The lower limit threshold value Ds is a value for discriminating that the edge portion image 70b is brighter than the central portion image 70a, and the upper limit threshold value De is a value for discriminating that the edge portion image 70b does not cause halation. The suppression coefficient C is calculated using a proportional relationship in which the suppression coefficient C is a larger value as the value of the brightness information D(n) increases in the range of the lower limit threshold value Ds to the upper limit threshold value De. The suppression coefficient C is a coefficient for suppressing the change amount or the change rate of the exposure amount in the exposure amount control.

The maximum value of the suppression coefficient C is a preset Cmax, and in a case in which the brightness information D(n) reaches a value equal to or greater than the upper limit threshold value De, the calculated suppression coefficient C is uniformly Cmax. In a case in which the brightness information D(n) is smaller than the lower limit threshold value Ds of the proportional range, the suppression coefficient C is set to 1, and in a case in which the brightness information D(n) is larger than the upper limit threshold value De of the proportional range, the suppression coefficient C is set to Cmax. The larger the value of the suppression coefficient C, the more gradual the change in the exposure amount due to the exposure amount control. In addition, even in a case in which the brightness information D(n) is a value outside the proportional range, the control content of the exposure amount is changed.

The suppression coefficient C is for suppressing the exposure amount control and is not for stopping the exposure amount control, so that the maximum value Cmax of the suppression coefficient C is a value for causing the exposure amount control to be executed at least once in the decided tracking pattern until the next control cycle. For example, in a case in which the brightness information calculation is performed every 1 second, the maximum value Cmax is a value at which the exposure amount control is performed in the decided tracking pattern at least once every 1 second. The value of Cmax fluctuates depending on the imaging conditions or the performance of the endoscope system 10.

Although it is preferable to execute the brightness information calculation each time the endoscope image 70 is acquired, since the brightness information calculation is also affected not only by the frame rate but also by the performance of equipment configuring the endoscope system 10 and the imaging conditions, a plurality of frames may be imaged during one control cycle T(n), such as calculation of the suppression coefficient C for each of five times of frame imaging of the endoscope image 70. In addition, the suppression coefficient C may be decided based on a transformation table (not shown) calculated in advance or the like, which is different from the relationship shown in FIG. 7.

The exposure amount control is performed by applying the decided suppression coefficient C, but the exposure amount to be changed in the exposure amount control can also be decided by using the high-brightness pixel. For example, the brightness of the endoscope image 70 may be discriminated by calculating a total value of the high-brightness pixels such as Xa+Xb in the calculation of the brightness information D(n). In addition, a degree of excess or deficiency of the exposure amount with respect to the endoscope image 70 can be discriminated from the change in the distribution of the histograms of FIG. 4A and FIG. 4B. It can be discriminated that the endoscope image 70 is insufficient in the exposure amount and is a dark image in a case in which the number of pixels of the group having a high brightness value is reduced and the number of pixels of the group having a low brightness value is increased.

Figure 8A:
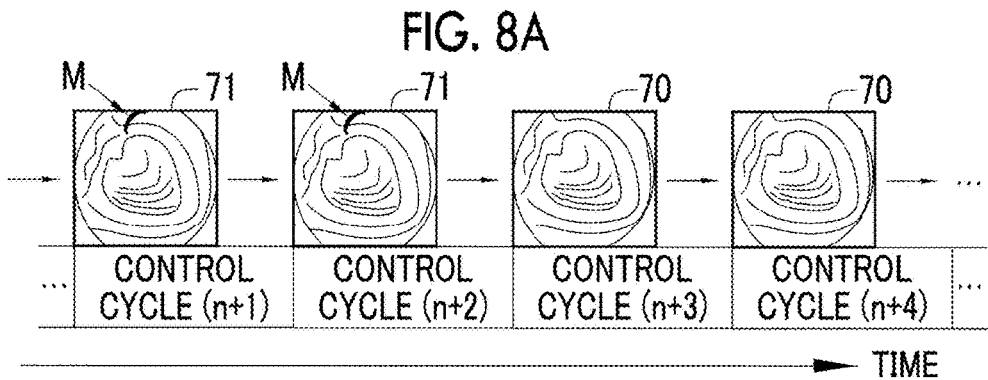
FIG. 8A is a time series explanatory diagram regarding a control cycle in endoscopic observation.
Figure 8B:
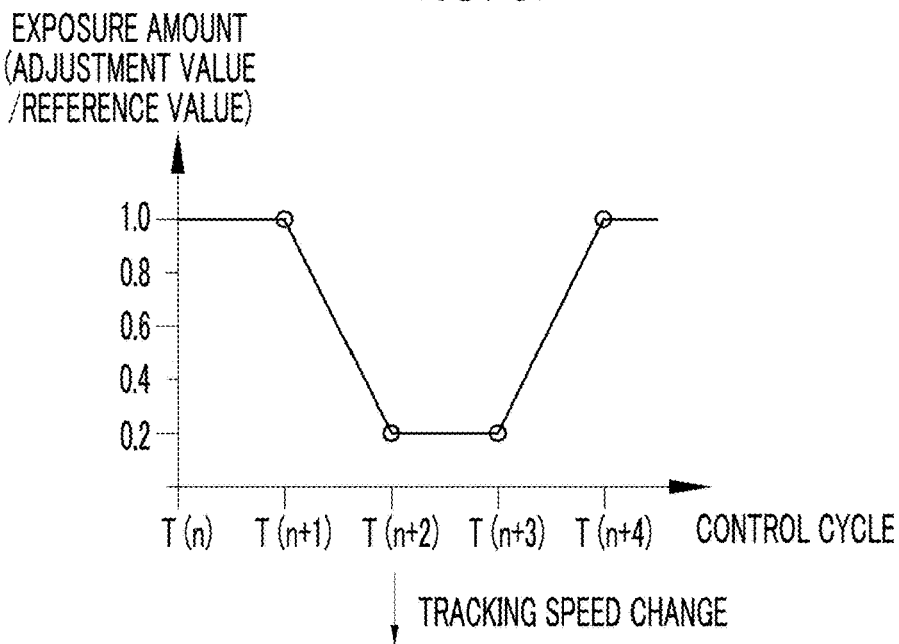
FIG. 8B is an explanatory diagram showing a relationship between an exposure amount and a control cycle in exposure amount control in a normal mode.
Figure 8C:
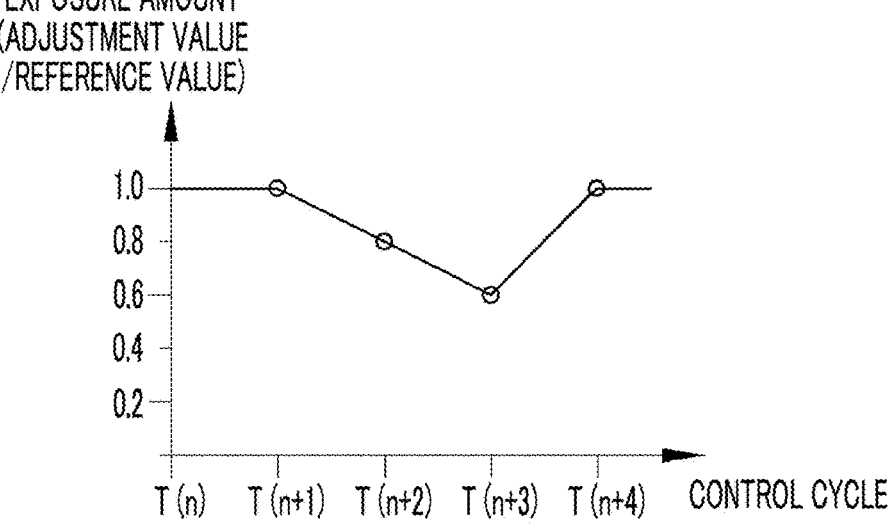
FIG. 8C is an explanatory diagram showing a relationship between an exposure amount and a control cycle in a tracking control mode by using a suppression coefficient.

As shown in FIG. 8, exposure amount control in a case in which a large amount of high-brightness pixels are generated in the edge portion image 70b, such as generation of halation in real-time observation, will be described. (A) of FIG. 8 is a transition of a control cycle in which a foreign substance M is reflected in the endoscope image 70 in the control cycle T(n+1) and the control cycle T(n+2), (B) of FIG. 8 is a graph showing a relationship between the exposure amount (vertical axis) and the transition of the control cycle (horizontal axis) in the normal mode, which corresponds to (A) of FIG. 8, and (C) of FIG. 8 is a graph showing a relationship between the exposure amount (vertical axis) and the transition of the control cycle (horizontal axis) in the tracking control mode, which corresponds to (A) of FIG. 8.

As shown in (A) of FIG. 8, the control cycle T(n+1) in which an endoscope image 71 in which the foreign substance M is reflected is captured, the control cycle T(n+2), and the control cycle T(n+3) in which the endoscope image 70 in which the foreign substance M is not reflected is captured are set. The control cycle after the control cycle T(n+3) is T(n+4), and the control cycle further continues thereafter. T(n) does not reflect an object such as the foreign substance M that causes adjustment of the exposure amount in the observation, and the exposure amount is a reference value for the average condition.

The transition of the exposure amount in the normal mode of (B) of FIG. 8 and the tracking control mode of (C) of FIG. 8 will be described using a reference value and an adjustment value which is a value of the exposure amount set based on the brightness information. The reference value of the exposure amount is defined as the exposure amount in the control cycle T(n) in which the endoscope image 70 in which the foreign substance M before the control cycle T(n+1) is not reflected and a specific exposure amount control operation is not performed is captured. That is, the exposure amount is described in terms of a relative change amount. The control of the exposure amount based on a change in the reflectivity for each imaging part or the like is omitted.

In the control cycle T(n+1) of the normal mode of (B) of FIG. 8, the exposure amount is decreased with respect to the reference value based on the brightness information of the endoscope image 71 in which the foreign substance M is reflected. For example, the exposure amount is adjusted to 20%. In the control cycle T(n+2), the imaging is performed with the exposure amount adjusted in the control cycle T(n+1), and the brightness information calculation is performed. Since the imaging is performed with the exposure amount corresponding to the foreign substance M, in the brightness information calculation, the exposure amount adjusted in the control cycle T(n+1) is maintained in a case in which the brightness of each pixel is distributed appropriately. The exposure amount during halation is appropriately adjusted to 10%, 25%, or the like depending on the situation.

The endoscope image 70 captured in the control cycle T(n+3) is in a state in which an imaging range is moved and the foreign substance M is not reflected, and the brightness value of the endoscope image 70 is a low value as a whole. Therefore, the exposure amount is adjusted to provide an appropriate distribution. For example, the exposure amount is changed to be the same as the control cycle TO. In a case in which there is no foreign substance even in the control cycle T(n+4), the exposure amount is not decreased.

In the normal mode, the exposure amount control is performed for each control cycle, so that the value of the brightness information D(n) of the endoscope image 70 is rapidly increased due to the occurrence of halation caused by the foreign substance M or the like, and the exposure amount control is executed in response to the increase in the value. In such a case, since the exposure amount control is extremely performed in a short time, a burden on the equipment is large, and a lifetime of a component may be shortened. In addition, the endoscope image 70 acquired by the imaging with the exposure amount control according to the foreign substance M may be in a state unsuitable for the observation.

In the tracking control mode of (C) of FIG. 8, in the control cycle T(n+1), the suppression coefficient C is calculated and the exposure amount control is performed based on the brightness information of the endoscope image 70 in which the foreign substance M is reflected. In a case in which the maximum value Cmax of the suppression coefficient C with respect to the halation is set to 4, the tracking speed (tracking rate) of the exposure amount control is ¼ with respect to the normal mode, and the exposure amount during the imaging in the control cycle T(n+2) is 0.8 because the change is ¼ with respect to the normal mode.

In a case in which the halation occurs even in the control cycle T(n+2), the brightness information D(n+2) is higher than the past brightness information Dp(n+1) and is equal to or greater than the upper limit threshold value De, and the suppression coefficient C is 4, which is the maximum value Cmax, as in the control cycle T1. In that case, the exposure amount during the imaging in the control cycle T(n+3) is 0.6.

On the other hand, in a case in which the halation does not occur in the imaging in the control cycle T(n+3), the brightness information D(n+3) is lower than the past brightness information Dp(n+2), so that the suppression coefficient C is reset, and the normal exposure amount control is performed. That is, the exposure amount is restored to a state in which the foreign substance M is not reflected until the imaging of the next control cycle T(n+4). Therefore, the exposure amount is increased.

It should be noted that, in the tracking control mode, the decrease in the exposure amount from 1.0 to 0.2 takes more time than in the normal mode depending on the value of the suppression coefficient C. For example, in the case of (C) of FIG. 8, in a case in which the endoscope image 71 in the halation state is continuously captured even in the control cycles T(n+3) to T(n+4), the exposure amount is 0.2 in the imaging of the control cycle T(n+5). In a case in which the endoscope image 71 is detected even in the control cycle T(n+5), the exposure amount can be further decreased, but is not decreased to 0.

The control cycle is a set of the image acquisition, the brightness information calculation, the brightness information comparison, the suppression coefficient calculation, the exposure amount control, and the past brightness information update. (C) of FIG. 8 is an exposure amount change in a case in which the maximum value Cmax of the suppression coefficient C to be changed is set to 4.0. On the other hand, the increase method in a case of increasing the value of Cmax or the exposure amount according to the performance of the endoscope system 10 or the observation situation, that is, the tracking pattern may be appropriately set.

In the change of the tracking speed using the calculated suppression coefficient C, in a case in which the tracking speed is brought close to 1, the correction of decreasing the value of the suppression coefficient C in a stepwise manner can be executed. The correction of the suppression coefficient C is preferably changed in a stepwise manner, and the change amount may be equally divided, or the tracking speed may be changed at a specific ratio. As a result, in the exposure amount control, it is not necessary to significantly change the amount of emitted light or the imaging parameter at once, so that a burden on each equipment of the endoscope system, such as the light source device 12, the endoscope 11, and the processor device 13, can be reduced even in a case in which the exposure amount is increased.

Figures 9A, 9B:
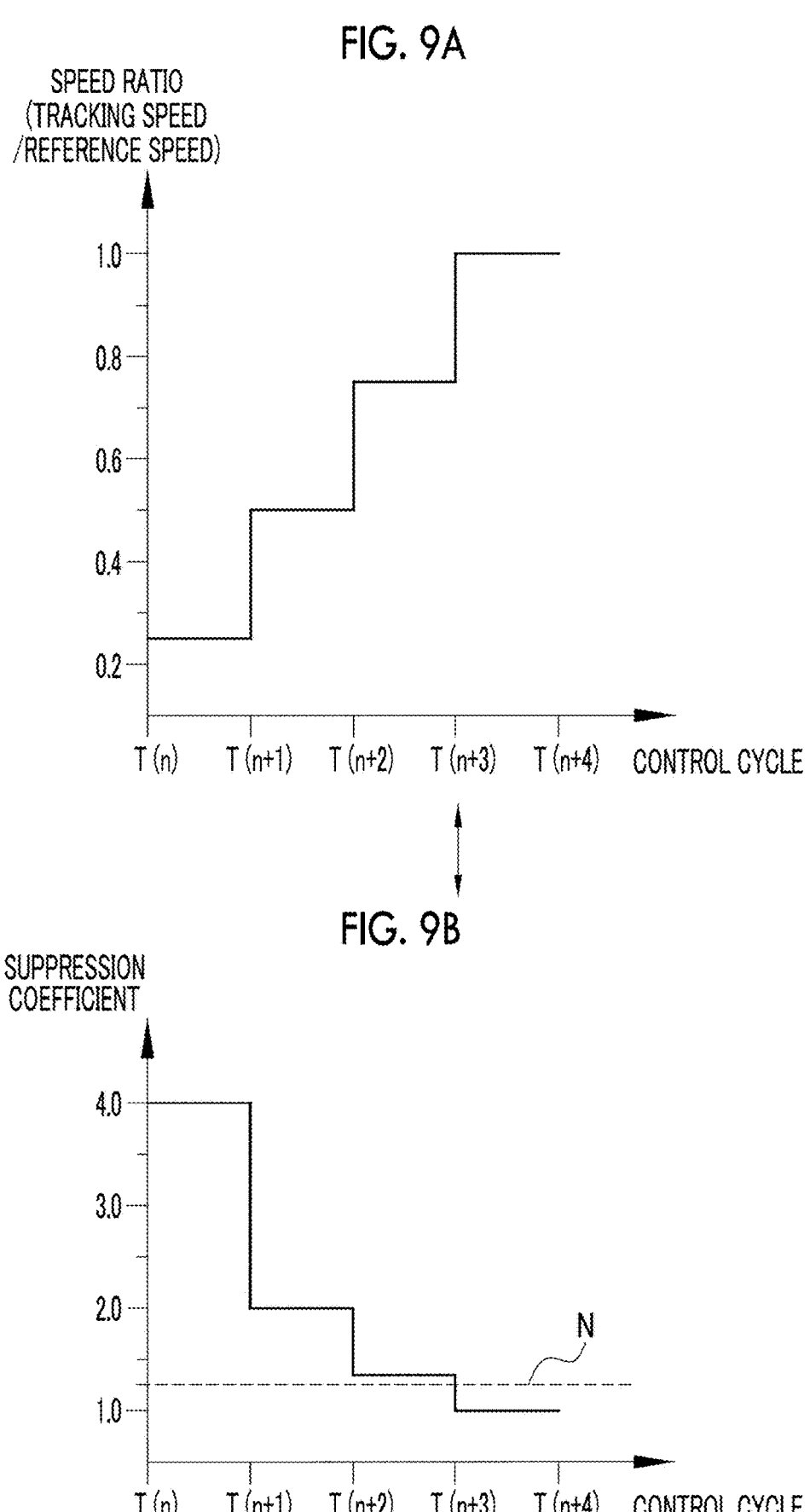
FIG. 9A is an explanatory diagram showing a change in a ratio of a tracking speed to a reference speed for each control cycle in a case in which a suppression coefficient is decreased.
FIG. 9B is an explanatory diagram showing a change in the suppression coefficient for each control cycle in a case in which the suppression coefficient is decreased.

In FIG. 9, the reset of the stepwise tracking speed in a case in which the tracking speed is set to 0.25 with the suppression coefficient C being Cmax=4 in the control cycle T(n) is described. The reset of the suppression coefficient C performed in a case in which the calculated brightness information D(n) is not brighter than the past brightness information Dp(n−1) is performed in a stepwise manner. That is, the correction of bringing the tracking speed closer to the reference state is performed. It is preferable that the amount of change at one time is appropriately decided by using the time until the next control cycle or the number of frames.

(A) of FIG. 9 is a graph showing a relationship between a ratio of the tracking speed to the speed in the reference state, which is the reciprocal of the suppression coefficient (vertical axis), and the transition of the control cycle (horizontal axis), and in a case in which the tracking speed is restored to the original state at equal intervals for each control cycle, for example, 0.25 for each control cycle, the tracking speed is restored to 0.5 in the control cycle T(n+1), 0.75 in the control cycle T(n+2), and 1.0 in the control cycle T(n+3).

In (B) of FIG. 9, a graph showing a relationship between the suppression coefficient C (vertical axis) and the transition of the control cycle (horizontal axis) is shown, and a stepwise change in the reset of the suppression coefficient C is shown. Since the tracking speed is reset to the reference state in a stepwise manner at equal intervals, the suppression coefficient C is changed in accordance with the tracking speed. The suppression coefficient C is restored to 2.0 in the control cycle T(n+1), 1.33 in the control cycle T(n+2), and 1.0 in the control cycle T(n+3).

The suppression coefficient C may be decreased by any value instead of the tracking speed. Even in that case, the stage of the change can be optionally set. In addition, since the suppression coefficient C is applied in order to perform the observation with appropriate brightness, in a case in which a value larger than a lower limit value is set, a threshold value N for discriminating whether the value has an effect on the appropriate observation with respect to the exposure amount control is set in advance. Therefore, in a case in which the suppression coefficient C is less than the threshold value N, the suppression coefficient C is set to the lower limit value. In (B) of FIG. 9, the threshold value N is set to 1.25, but may be set to 1.20, 1.10, or the like as appropriate.

The control of the light emission controller 22 and the exposure amount controller 60 in the normal mode and the tracking control mode is control of single-frame observation using a single light source, but may be control of multi-frame observation in which the amount of light emitted in a case in which a plurality of light sources are turned on or off is independently controlled. The type and the number of the light sources are different depending on the light source unit 20.

In the multi-frame observation mode, multi-frame light emission is performed in which a plurality of illumination light beams are switched on and off in a preset pattern. For example, in a case in which first illumination light and second illumination light are used, one of first illumination light and second illumination light may be broadband light and the other may be special light, or a combination of the first illumination light and the second illumination light may be used to obtain broadband light. Wavelength ranges of the first illumination light and the second illumination light may be different from each other or may be the same as each other.

In any light emission pattern, the observation target is illuminated with illumination light of each frame, an image is captured by the imaging sensor 44 to acquire a captured image, and one observation image is generated using a plurality of captured images having different illumination light beams. In the multi-frame observation mode, one observation image can be generated from captured images of frames in which different illumination light beams are consecutively emitted, for example, a captured image of an N-th frame and a captured image of an (N+1)th frame. Another method may be used as a method of generating the observation image from the plurality of captured images.

Figure 10:
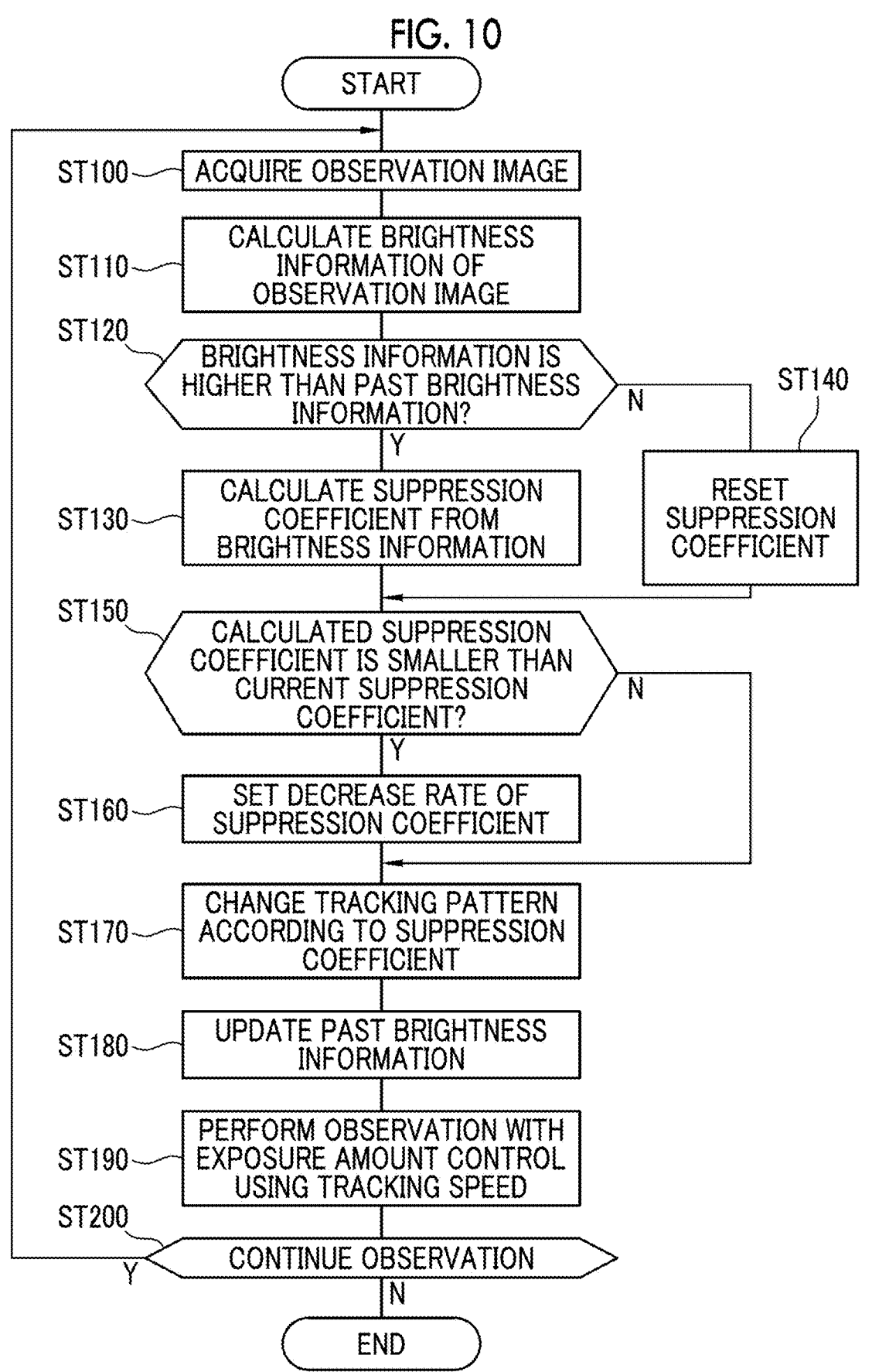
FIG. 10 is a flowchart showing a series of flows of exposure amount control according to a tracking speed in the present invention.

A series of flows of operations in one control cycle in the tracking control mode of the present embodiment will be described with reference to a flowchart shown in FIG. 10. The endoscope system 10 sets the observation mode to the tracking control mode, starts the exposure amount control in which the tracking speed based on the suppression coefficient C is applied, and acquires the observation image (step ST100). In a case in which the suppression coefficient C is not calculated, the suppression coefficient C is set to the lower limit value, and the observation is performed in the reference state with the same tracking speed as the normal mode. The exposure amount controller 60 calculates the brightness information from the acquired observation image (step ST110).

The calculated brightness information is compared with the past brightness information to discriminate whether or not the calculated brightness information is higher than the past brightness information (step ST120). In a case in which the calculated brightness information is brighter than the past brightness information in the comparison of the brightness information (Y in step ST120), the suppression coefficient C is calculated based on the brightness information (step ST130). In a case in which the calculated brightness information is not brighter than the past brightness information in the comparison of the brightness information (N in step ST120), the suppression coefficient C is reset, that is, set to a value that is not suppressed (step ST140).

The suppression coefficient C and the suppression coefficient C at the current tracking speed are compared with each other (step ST150). In a case in which the calculated suppression coefficient C is larger than the current suppression coefficient C (N in step ST150), the suppression coefficient C is set as it is. On the other hand, in a case in which the calculated suppression coefficient C is smaller than the current suppression coefficient C (Y in step ST150), a decrease rate of the suppression coefficient C is set (step ST160).

The tracking speed in the exposure amount control is changed according to the set suppression coefficient C (step ST170). After the decision of the tracking speed, the past brightness information is updated based on the calculated brightness information (step ST180). The observation is performed with the exposure amount control using the changed tracking speed (step ST190). In a case in which the observation is continued in the tracking control mode (Y in step ST200), the endoscopic observation is performed with the exposure amount control using the changed tracking speed, and the observation image is captured (step ST100). In a case in which the observation is not continued in the tracking control mode (N in step ST200), the tracking control mode is switched to the normal mode. The endoscopic observation may be ended as it is instead of switching to the normal mode.

In the above-described example, the exposure amount controller 60 that calculates the brightness information from the brightness information D(n) of the number of high-brightness pixels of the central portion image 70a and the edge portion image 70b has been described, but the exposure amount control of calculating the brightness information from a proportion of the number of high-brightness pixels of the edge portion image 70b may be executed. Hereinafter, a modification example of performing the calculation using the proportion of the number of high-brightness pixels will be described.

The brightness information is calculated using the proportion of the number of high-brightness pixels of the edge portion image 70b to the entire image. In the above-described example, an area ratio between the central portion image 70a to the edge portion image 70b is 1:1, that is, an area ratio between the endoscope image 70 and the edge portion image 70b is 2:1, but the brightness information may be calculated with an area ratio other than this.

Figure 11A:
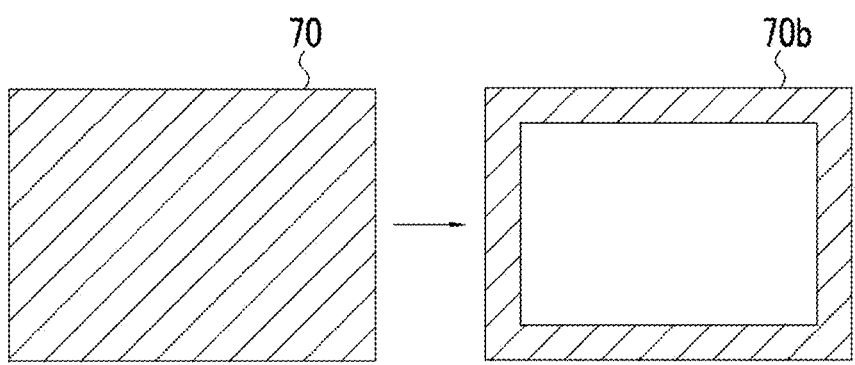
Figure 11B:
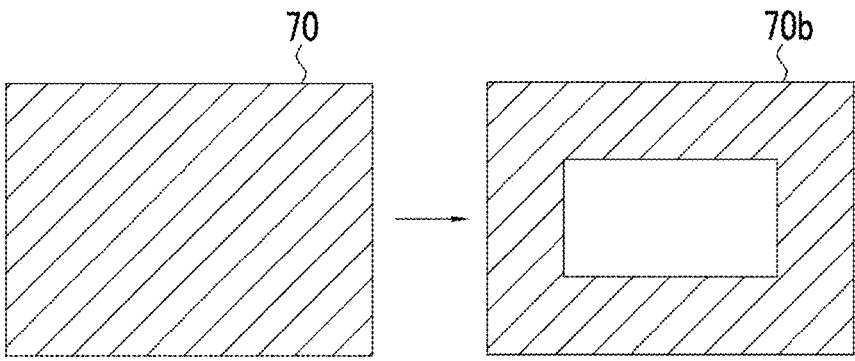

As shown in FIGS. 11A and 11B, the exposure amount control is performed at a tracking speed decided by dividing a region of the endoscope image 70 to have any area ratio and calculating the brightness information. For example, the area ratio can be set depending on whether to prioritize the speed or sensitivity or the accuracy in the change in the tracking speed. As shown in FIG. 11A, as the area occupied in the edge portion is smaller, such as setting an area ratio of the endoscope image 70 to the image edge portion to 4:1, the change of a small number of pixels to the high-brightness pixel affects the brightness information, so that foreign substance causing the halation can be detected in an early control cycle. On the other hand, as shown in FIG. 11B, as the area occupied in the edge portion image 70b is larger, such as setting an area ratio of the endoscope image 70 to the edge portion image 70b to 3:2, a larger number of pixels are required to affect the brightness information, so that foreign substance causing the halation can be detected at high accuracy.

In the above embodiment, the hardware structure of a processing unit that executes various kinds of processing, such as the light emission controller 22, the imaging controller 45, the image signal acquisition unit 50, the DSP 51, the noise reduction unit 52, the image processing unit 53, the output controller 54, and the exposure amount controller 60. The various processors include a central processing unit (CPU) that is a general-purpose processor that executes software (programs) to function as various processing units, a graphical processing unit (GPU), a programmable logic device (PLD) that is a processor capable of changing a circuit configuration after manufacture, such as a field programmable gate array (FPGA), and an exclusive electric circuit that is a processor having a circuit configuration exclusively designed to execute various kinds of processing.

One processing unit may be configured of one of these various processors, or may be configured of a combination of two or more processors of the same type or different types (for example, a plurality of FPGAs, a combination of a CPU and an FPGA, or a combination of a CPU and a GPU). In addition, a plurality of processing units may be configured of one processor. As an example in which the plurality of processing units are configured of one processor, first, as typified by computers such as a client or a server, one processor is configured of a combination of one or more CPUs and software, and this processor functions as the plurality of processing units. Second, as typified by a system on chip (SoC) or the like, a processor that realizes the functions of the entire system including the plurality of processing units by using one integrated circuit (IC) chip is used. As described above, the various processing units are configured using one or more of the various processors as a hardware structure.

Furthermore, the hardware structure of the various processors is more specifically an electric circuit (circuitry) having a form in which circuit elements such as semiconductor elements are combined. In addition, a hardware structure of a storage unit is a storage device such as a hard disc drive (HDD) or a solid state drive (SSD). In addition, from the above description, it is possible to grasp the endoscope system described in Appendices 1 to 12.

APPENDIX 1

An endoscope system comprising:
a processor,
in which the processor
  performs exposure amount control based on an endoscope image captured by an endoscope including an imaging element,
  calculates brightness information indicating a degree of brightness of an edge portion of the endoscope image, and
  controls a tracking speed of the exposure amount control based on the brightness information.

APPENDIX 2

The endoscope system according to Appendix 1,
in which the processor
  calculates a suppression coefficient for suppressing a change amount or a change rate of an exposure amount in the exposure amount control based on the brightness information, and
  applies the suppression coefficient to the exposure amount control to control the tracking speed.

APPENDIX 3

The endoscope system according to Appendix 2,
in which the processor decides the suppression coefficient according to a comparison result of past brightness information, which is the brightness information in the past, and the brightness information.

APPENDIX 4

The endoscope system according to Appendix 3,
in which the processor calculates the suppression coefficient in a case in which the brightness information is larger than the past brightness information in the comparison result.

APPENDIX 5

The endoscope system according to Appendix 3 or 4,
in which the processor sets the suppression coefficient to a lower limit value in a case in which the brightness information is equal to or less than the past brightness information in the comparison result.

APPENDIX 6

The endoscope system according to any one of Appendices 2 to 5,
in which the processor
  holds a pre-change suppression coefficient, which is the suppression coefficient used for calculating the tracking speed before change, and
  performs correction of the suppression coefficient in a case in which the suppression coefficient is smaller than the pre-change suppression coefficient.

APPENDIX 7

The endoscope system according to Appendix 6,
in which the processor performs a change of bringing the tracking speed closer to a reference state in a stepwise manner as the correction.

APPENDIX 8

The endoscope system according to Appendix 5,
in which the processor sets the suppression coefficient to the lower limit value in a case in which the suppression coefficient is equal to or less than a preset threshold value.

APPENDIX 9

The endoscope system according to any one of Appendices 3 to 8,
in which the processor updates the past brightness information by using the calculated brightness information and a plurality of pieces of the past brightness information held.

APPENDIX 10

The endoscope system according to any one of Appendices 1 to 9,
in which the processor calculates the brightness information from a difference in brightness between a central portion of the endoscope image and the edge portion of the endoscope image.

APPENDIX 11

The endoscope system according to any one of Appendices 1 to 10,
in which the processor decides the brightness information based on an amount of high-brightness pixels, which are pixels having a brightness value equal to or greater than a preset threshold value.

APPENDIX 12

The endoscope system according to any one of Appendices 1 to 11,
in which the processor changes at least any of an amount of illumination light or an imaging parameter of the imaging element based on the brightness information as the exposure amount control.

EXPLANATION OF REFERENCES

10: endoscope system
11: endoscope
11$a$: insertion part
11$b$: operation part
11$c$: bendable part
11$d$: distal end part
11$e$: mode selector switch
12: light source device
13: processor device
14: display
15: user interface
20: light source unit
22: light emission controller
29: light guide
30: illumination optical system
32: illumination lens
40: imaging optical system
42: objective lens
44: imaging sensor
45: imaging controller
46: CDS/AGC circuit
48: A/D converter
50: image signal acquisition unit
51: DSP
52: noise reduction unit
53: image processing unit
54: output controller
60: exposure amount controller
61: brightness information calculation unit
62: brightness information holding unit
63: brightness information comparison unit
64: suppression coefficient calculation unit
65: tracking pattern decision unit
66: brightness information update unit
70: endoscope image
70$a$: central portion image
70$b$: edge portion image
71: endoscope image
ST100 to ST200: step
A1 to A8: group
B1 to B8: group
D(n): brightness information
M: foreign substance
N: threshold value

What is claimed is:
1. An endoscope system comprising:
a processor,
wherein the processor
performs exposure amount control based on an endoscope image captured by an endoscope including an imaging element,
calculates brightness information indicating a degree of brightness of an edge portion of the endoscope image, wherein the processor calculates the brightness information from a difference in brightness between a central portion of the endoscope image and the edge portion of the endoscope image, and
controls a tracking speed of the exposure amount control based on the brightness information.
2. The endoscope system according to claim 1,
wherein the processor
calculates a suppression coefficient for suppressing a change amount or a change rate of an exposure amount in the exposure amount control based on the brightness information, and
applies the suppression coefficient to the exposure amount control to control the tracking speed.
3. The endoscope system according to claim 2,
wherein the processor decides the suppression coefficient according to a comparison result of past brightness information, which is the brightness information in the past, and the brightness information.
4. The endoscope system according to claim 3,
wherein the processor calculates the suppression coefficient in a case in which the brightness information is larger than the past brightness information in the comparison result.
5. The endoscope system according to claim 3,
wherein the processor sets the suppression coefficient to a lower limit value in a case in which the brightness information is equal to or less than the past brightness information in the comparison result.
6. The endoscope system according to claim 5,
wherein the processor
holds a pre-change suppression coefficient, which is the suppression coefficient used for calculating the tracking speed before change, and performs correction of the suppression coefficient in a case in which the suppression coefficient is smaller than the pre-change suppression coefficient.

7. The endoscope system according to claim 6, wherein the processor performs a change of bringing the tracking speed closer to a reference state in a stepwise manner as the correction.

8. The endoscope system according to claim 5, wherein the processor sets the suppression coefficient to the lower limit value in a case in which the suppression coefficient is equal to or less than a preset threshold value.

9. The endoscope system according to claim 3, wherein the processor updates the past brightness information by using the calculated brightness information and a plurality of pieces of the past brightness information held.

10. The endoscope system according to claim 1, wherein the processor decides the brightness information based on an amount of high-brightness pixels, which are pixels having a brightness value equal to or greater than a preset threshold value.

11. The endoscope system according to claim 1, wherein the processor changes at least any of an amount of illumination light or an imaging parameter of the imaging element based on the brightness information as the exposure amount control.

12. A method of operating an endoscope system, the method comprising:
a step of capturing an endoscope image based on exposure amount control;
a step of calculating brightness information indicating a degree of brightness of an edge portion of the endoscope image, wherein the brightness information is calculated from a difference in brightness between a central portion of the endoscope image and the edge portion of the endoscope image; and
a step of controlling a tracking speed of the exposure amount control according to the brightness information.

* * * * *